United States Patent
Haeusler et al.

[11] Patent Number: 6,002,702
[45] Date of Patent: Dec. 14, 1999

[54] RADIATION SOURCE FOR LASER SPECTROSCOPY

[75] Inventors: Andrea Haeusler, Hamburg; Günter Steinert, Bad Oldesloe, both of Germany

[73] Assignee: Dragerwerk AG, Lubeck, Germany

[21] Appl. No.: 08/984,267

[22] Filed: Dec. 3, 1997

[30] Foreign Application Priority Data

Jun. 21, 1997 [DE] Germany .......................... 197 26 455

[51] Int. Cl.⁶ ..................................................... H01S 3/19
[52] U.S. Cl. ................................ 372/50; 372/26; 372/28; 356/346; 359/254; 422/91
[58] Field of Search ............................... 372/20, 26, 28, 372/29, 31, 32, 34, 38, 50, 98; 250/231.11, 225; 356/346; 422/89, 91, 88; 359/248, 254

[56] References Cited

U.S. PATENT DOCUMENTS

| | | | |
|---|---|---|---|
| 4,934,816 | 6/1990 | Silver et al. | 356/409 |
| 5,331,658 | 7/1994 | Shieh et al. | 372/50 |
| 5,411,709 | 5/1995 | Furuki et al. | 422/91 |
| 5,698,847 | 12/1997 | Yoda et al. | 250/225 |

*Primary Examiner*—Hemang Sanghavi
*Attorney, Agent, or Firm*—McGlew and Tuttle, P.C.

[57] ABSTRACT

A laser array for determining the concentrations of gases. A simply acting device and a corresponding process are provided, which make possible a high signal resolution by reducing the interferences without prolonging the measurement time. The interferences occurring in the laser array are reduced by the laser source being set to perform longitudinal oscillations in the direction of the optical axis. These oscillations preferably have a sinus or sawtooth shape, and a frequency in the range of 10 to 1,000 Hz that does not otherwise occur in the laser array and an oscillation amplitude corresponding to one fourth to a multiple of the wavelength of the radiation of the laser source.

10 Claims, 1 Drawing Sheet

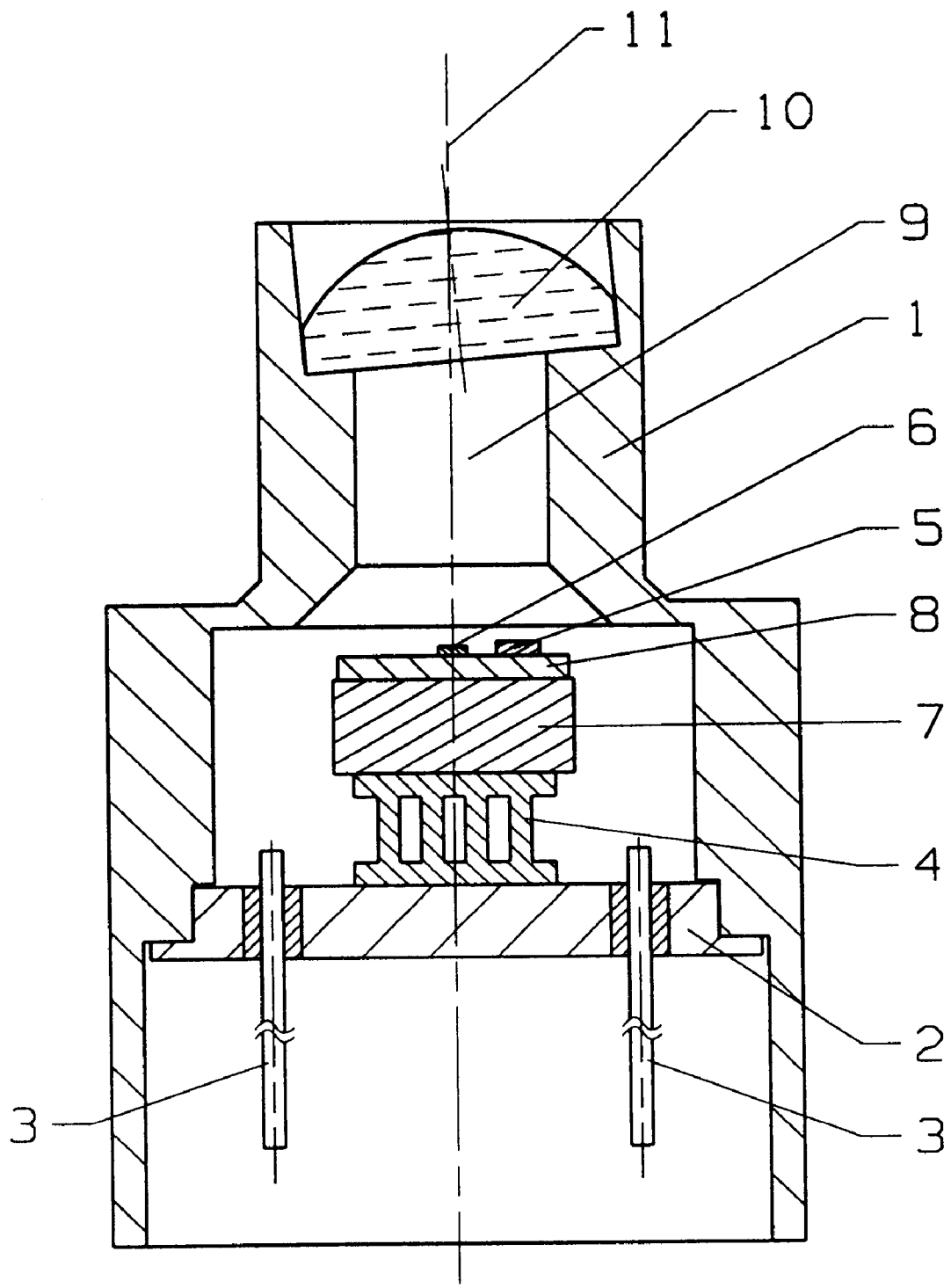

RADIATION SOURCE FOR LASER SPECTROSCOPY

FIELD OF THE INVENTION

The present invention pertains to a laser array for determining the concentrations of gases.

BACKGROUND OF THE INVENTION

Such measuring arrays, e.g., in the form of a sensor, are used to determine the concentration of a gas, e.g., oxygen, in a mixture with other gases based on the radiation absorption, which is characteristic of the particular substance and is concentration-dependent. Such an optical measuring array contains as its essential elements one or more laser sources, optical elements for guiding the beam, as well as a measured gas sample holder and one or more radiation detectors.

Interferences, which markedly limit the sensitivity of such an optical measuring array, are generated by multiple reflections of the laser beam on surfaces positioned between laser sources and radiation detectors. It has been known that this adverse effect can be markedly reduced by obliquely positioning the optical elements in the beam path. However, this measure is insufficient for improving the signal resolution in the case of a high-resolution system with weak absorptions, such as that of oxygen. In addition, a lengthy averaging of the signals, which would also reduce the effect of the interferences, is not possible in the field of medicine, because rapid signal rise times are desirable for measurements that are resolved for individual breaths.

Various suggestions have been made to improve the sensitivity of sensors and the resolution of the measured signal. One prior-art solution is to increase the length of the absorption path. To nevertheless prevent an impairment in the time resolution, the volume of the gas sample holder must be maintained, i.e., the diameter of the sample holder must be markedly reduced. This leads to problems in focusing and guiding the laser beam.

An array for averaging out the interferences has become known from U.S. Pat. No. 4,934,816. The essential component of this prior-art array is an active optical element, which is arranged in the course of the beam path and oscillates along the optical path. The drawback of this prior-art array is the technical effort needed to achieve the tightness of the absorption cell with the oscillating optical element, on the one hand, and additional transmission losses which due to the necessary multiple deflections of the laser beam, on the other hand.

SUMMARY AND OBJECTS OF THE INVENTION

The primary object of the present invention is to provide simply acting means and a corresponding process, which make possible a high signal resolution without prolongation of the measurement time for a laser array for determining the concentration of a gas.

According to the invention, a laser array is provided for determining the concentrations of gases. At least one laser source is connected to longitudinal oscillation means which imposes on the laser source longitudinal oscillations in the range of 10 to 1,000 Hz with an amplitude of at least one fourth the wavelength of the radiation of the laser source in the direction of the optical axis.

The longitudinal oscillation means preferably imposes longitudinal oscillations in parallel to the optical axis to the laser source. The oscillations have frequencies that are asynchronous to all the modulation frequencies used in the laser array.

The laser source may be arranged on a ceramic support. The ceramic support may be connected to a Peltier element via one or more piezo oscillating elements arranged one on top of another. The laser source may be connected via the ceramic support to an oscillatingly mounted metal element, which imposes longitudinal oscillations in the direction of the optical axis via a controlled coil by periodically repelling and attracting the laser source. The laser source may be connected via the ceramic support to an oscillatingly mounted bimetal element, which imposes longitudinal oscillations in the direction of the optical axis via a periodic temperature control and the resulting deflections of the laser source.

The longitudinal oscillations may have a sawtooth or sinus shape.

The invention also includes a process according for operating an array. The laser source may be set to perform longitudinal oscillations in the direction of the optical axis, wherein the longitudinal oscillations have a preferably sinus or sawtooth shape and frequencies of 10 to 1,000 Hz that do not otherwise occur in the laser array, and an oscillation amplitude corresponding to at least one fourth the wavelength of the radiation of the laser source.

One essential advantage of the present invention compared with the state of the art is that embodiment is possible with relatively simple means and that the optical design of the measuring array in the beam path does not have to be changed. No additional elements, which would inherently lead to an increase in the transmission losses, are introduced into the beam path. The core of the present invention is to set the laser source to oscillate in the direction of the optical axis or to suggest means suitable for this purpose, wherein the amplitude of the oscillations is on the order of magnitude of the wavelength of the laser source and is preferably one fourth to a multiple of the wavelength of the laser light. A measured signal resolution of about 0.1 vol. % is necessary for measuring the oxygen concentration in the breathing gas resolved for individual breaths in medical technology. This cannot practically be achieved due to the interferences usually occurring in optical measuring arrays with a laser source, which lead to increased noise during the absorption measurement. The resolution of the measured signal is increased by up to 300% with the laser array according to the present invention and the process according to the present invention due to an extensive reduction in the interferences occurring in the optical system compared with an otherwise identical measuring array with a laser source not set to perform longitudinal oscillations in relation to the optical axis. The position of the radiation source is changed oscillatingly relative to all other optical elements in the design of the laser array. Interferences between fixed surfaces, such as lenses, and moving surfaces, such as laser sources or a laser chip on a corresponding ceramic support, are practically eliminated by a rapid periodical movement of the laser source at a frequency of about 10 to 1,000 Hz along the optical axis as well as by an averaging over time of the detector signal. Interferences between two fixed surfaces can be additionally reduced by these surfaces, especially lenses, being provided with suitable, reflection-reducing coatings and being additionally positioned obliquely in relation to one another. The oscillation of the laser beam along the optical axis takes place preferably asynchronously to all the modulation frequencies used in the laser array and it leads to the extinction of the amplitudes of the interference fringes if the path traveled during the oscillation causes a change in the optical path length by more than half of the spectral range free from the interference fringe. In terms of a device, the present invention is embodied such that relatively slight requirements need to be imposed on the oscillating system: High requirements are not imposed on the accuracy and the constancy of the oscillation amplitude and the oscillation frequency. An oscillation amplitude approximately corresponding to the wavelength of the radiation emitted by the laser source and a frequency in the range of preferably 10 to 1,000 Hz are used, and the frequency used does not otherwise occur in the particular laser array. The deflection for the longitudinal oscillation of the laser source preferably has a sinus or especially sawtooth-shaped pattern. The requirements that need to be imposed especially in the case of high-resolution optical measuring arrays as well as rapid-resolution applications are met by the present invention. The temperature control of the laser source is also guaranteed with the array according to the present invention at the same time, which means low power loss, good thermal conductivity as well as good removal of the heat caused by the power loss of the Peltier element. Another advantage of the array according to the present invention is that stable positioning of the laser source and its encapsulation in a housing is possible due to the compact design. Finally, the low cost of embodying the present invention shall be mentioned, because it is possible, in principle, to use commercially available components and materials, so that an inexpensive mass production can be ensured. According to an advantageous embodiment of the present invention, the laser source or a plurality of laser sources are arranged in the form of a laser diode chip on a substrate element, preferably in the form of a ceramic support, which causes a change in the optical path length between the laser sources and all the optical elements following them in the beam path due to corresponding periodical longitudinal oscillations imposed by a piezo oscillating element.

The various features of the novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWING

In the drawing:

The only FIGURE is a sectional view of a device according to the invention.

DESCRIPTION OF THE PREFERRED EMBODIMENTS

Referring to the drawing in particular, a basic setup according to the present invention is shown. A base 2 is bonded in a housing 1 made of a plastic or metal with contact pins 3 for the electric power supply, not shown, and for the control of the components used. The Peltier element 4 bonded to the base 2 is used to set the temperature of the laser source, which is monitored with the temperature sensor 5, e.g., an NTC, according to the operating conditions. The piezo oscillating element 7, which may also consist of a plurality of individual elements arranged one on top of another to generate the desired oscillation amplitudes ranging from a few nanometers to micrometers, is preferably also connected to the Peltier element 4 with a prior-art thermocontact adhesive for good dissipation of heat. The ceramic support 8, which is likewise fastened to it with thermocontact adhesive, carries the laser source 6, the temperature sensor 5 as well as the corresponding electrical connection elements. The temperature of the laser source 6 can be controlled with the setup described with low power loss, good dissipation of heat and good dissipation of the heat generated by the power loss of the Peltier element 4. In a special application, the laser source 6 is designed as a chip with one or more, especially four laser diodes, wherein vertically emitting laser diodes, so-called VCSEL (Vertical Cavity Surface Emitting Laser Diodes), are especially preferred. The optical beam path changes in the overall array up to the radiation detector, not shown, due to the oscillation of the laser source 6 imposed by the piezo oscillating element 7 in the direction of the optical axis 11, so that the interferences occurring are averaged out almost completely and the signal resolution is correspondingly improved. An obliquely positioned lens 10 provided likewise to reduce interferences between fixed surfaces of the overall array is fitted into the closing cap of the housing 1. The closing cap of the housing 1, filled with a protective gas 9, is used to protect the laser source 6 and, due to the hermetic encapsulation, ultimately to prolong the service life of the laser diodes used. Instead of imaging on a radiation detector, it would also be possible to couple the laser light into an optical fiber after modifying the imaging element. Instead of the piezo oscillating element 7 generating longitudinal oscillations, it is also possible to use miniature magnets combined with coils, or bimetal elements carrying the laser source 6, which must be deflected corresponding to the desired periodical longitudinal oscillations in the direction of the optical axis 11 and be energized for this.

While specific embodiments of the invention have been shown and described in detail to illustrate the application of the principles of the invention, it will be understood that the invention may be embodied otherwise without departing from such principles.

What is claimed is:

1. The laser array for determining the concentrations of gases, the laser array comprising:

at least one laser source having an optical axis;

longitudinal oscillation means for imposing on said at least one laser source longitudinal oscillations in the range of 10 to 1,000 Hz with an amplitude of at least one fourth the wavelength of the radiation of said at least one laser source in a direction of said optical axis.

2. The laser array in accordance with claim 1, wherein said longitudinal oscillation means imposes oscillations in parallel to said optical axis to the said laser source, said oscillations having frequencies that are asynchronous to modulation frequencies used in the laser array.

3. The laser array in accordance with claim 1, further comprising:

a ceramic support wherein said laser source is arranged on said ceramic support, said longitudinal oscillation means including at least one piezo oscillating elements; and a Peltier element, said ceramic support being connected to said Peltier element via said at least one piezo oscillating element.

4. The laser array in accordance with claim 1, further comprising:

a piezo oscillating element as said longitudinal oscillation means.

5. The laser array in accordance with claim 4, further comprising:

one or more additional piezo oscillating elements, said piezo oscillating element and said one or more additional piezo oscillating elements being arranged one on top of another.

6. The laser array in accordance with claim 1, further comprising:
   an oscillatingly mounted metal element;
   a ceramic support wherein said laser source is arranged on said ceramic support, said laser source is connected via said ceramic support to said oscillatingly mounted metal element; and
   a controlled coil oscillatingly mounted metal element imposing longitudinal oscillations in the direction of said optical axis via said controlled coil by periodically repelling and attracting said laser source.

7. The laser array in accordance with claim 1, further comprising a ceramic support, said laser source being arranged on said ceramic support, said longitudinal oscillation means being an oscillatingly mounted bimetal element, which imposes longitudinal oscillations in the direction of said optical axis via a periodic temperature control and the resulting deflections of said laser source.

8. The laser array in accordance with claim 1, wherein the longitudinal oscillations have a sawtooth or sinus shape.

9. A process for reducing interferences in a laser array for determining the concentrations of gases, the process comprising the steps of:
   providing at least one laser source, the at least one laser source having an optical axis;
   imposing on said at least one laser source longitudinal oscillations in the direction of the optical axis, the longitudinal oscillations having frequencies of 10 to 1,000 Hz, and an oscillation amplitude corresponding to at least one fourth the wavelength of the radiation of the said laser source.

10. A process according to claim 9, wherein the longitudinal oscillations have a sinus or sawtooth shape.

* * * * *